(12) United States Patent
Muller (10) Patent No.: US 6,862,771 B1
(45) Date of Patent: Mar. 8, 2005

(54) TOOTHBRUSH HEAD WITH MEANS TO DIRECT AND COLLECT RADIATION

(75) Inventor: Werner Muller, Wetzlar-Nauborn (DE)

(73) Assignees: SmithKline Beecham GmbH & Co. KG, Wetzlar-Nauborn (DE); Helmut Hung GmbH, Wetzlar-Nauborn (DE)

( * ) Notice: Subject to any disclaimer, the term of this patent is extended or adjusted under 35 U.S.C. 154(b) by 0 days.

(21) Appl. No.: 09/762,022

(22) PCT Filed: Aug. 2, 1999

(86) PCT No.: PCT/EP99/05582

§ 371 (c)(1),
(2), (4) Date: Mar. 23, 2001

(87) PCT Pub. No.: WO00/07482

PCT Pub. Date: Feb. 17, 2000

(30) Foreign Application Priority Data

Aug. 5, 1998 (GB) ............................................. 9816914

(51) Int. Cl.[7] .............................. A61C 3/00; A46B 9/00
(52) U.S. Cl. .......................... 15/105; 15/167.1; 300/21; 264/243
(58) Field of Search ............................. 15/105, 167.1; 433/29, 215, 216; 300/21; 264/243

(56) References Cited

U.S. PATENT DOCUMENTS

| | | | | |
|---|---|---|---|---|
| 3,261,978 A | * | 7/1966 | Brenman ...................... 15/105 |
| 5,030,090 A | * | 7/1991 | Maeda et al. ................. 433/29 |
| 5,306,143 A | * | 4/1994 | Levy ............................ 433/29 |
| 5,382,163 A | * | 1/1995 | Putnam ........................ 433/29 |
| 5,658,148 A | * | 8/1997 | Neuberger et al. ............ 433/29 |
| 5,894,620 A | * | 4/1999 | Polaert et al. ................ 433/29 |
| 6,026,828 A | * | 2/2000 | Altshuler ..................... 433/29 |
| 6,029,304 A | * | 2/2000 | Hulke et al. .................. 15/105 |
| 6,343,400 B1 | * | 2/2002 | Massholder et al. .......... 15/105 |
| 6,485,300 B1 | * | 11/2002 | Muller et al. ................. 433/29 |

FOREIGN PATENT DOCUMENTS

| | | | |
|---|---|---|---|
| DE | 297 04 185 | * | 6/1997 |
| DE | 297 054 934 | | 6/1997 |
| EP | 0 593 375 A | | 4/1994 |
| EP | 0 774 235 | * | 5/1997 |
| WO | WO 92 06671 A | | 4/1992 |
| WO | WO 97 01298 | | 1/1997 |
| WO | WO-98/10711 | * | 3/1998 |
| WO | WO-99/59462 | * | 11/1999 |

* cited by examiner

*Primary Examiner*—Theresa T. Snider
(74) *Attorney, Agent, or Firm*—Nora Stein-Fernandez; Theodore R. Furman

(57) ABSTRACT

A toothbrush head suitable to direct incident radiation toward a surface of a tooth and to collect emitted radiation from the surface of the tooth, being made at least in past of a material which is transparent to the incident and/or emitted radiation. In preferred embodiments the head includes one or more radiation guiding cores of transparent material.

13 Claims, 10 Drawing Sheets

TOOTHBRUSH HEAD WITH MEANS TO DIRECT AND COLLECT RADIATION

FIELD OF THE INVENTION

This invention relates to toothbrushes. In particular this invention relates to toothbrushes having means for detecting plaque and other biological deposits on the surface of teeth by directing incident radiation onto the surface of the teeth and detecting fluorescence radiation emitted from the teeth in consequence.

BACKGROUND OF THE INVENTION

The term "biological deposits" used herein refers generally to deposits of material of biological origin, e.g. plaque, bacteria, tartar, calculus etc. which are generally regarded as undesirable for dental hygiene. Dental plaque is a complex organic deposit generated in part by the activity of bacteria upon the teeth or upon contamination, e.g. food deposits on the teeth, and is an undesirable precursor to tooth decay and the development of dental caries.

It is desirable to detect such deposits on the teeth before removing them, for example by toothbrushing, as detection indicates the areas at which dental cleaning effort should be concentrated. Such deposits can be difficult to detect in situ in vivo on the teeth. It is especially important to detect dental plaque. For detection of plaque it is known to use fluorescence measurement, in which incident radiation is directed at the surfaces of teeth, and fluorescence radiation having characteristics associated with the presence of biological deposits is emitted from the teeth and is detected.

In the state of the art there are two general methods for detecting dental plaque, using respectively primary fluorescence in which the fluorescence of dental plaque or other dental material itself is monitored, and secondary fluorescence in which teeth suspected of bearing plaque are treated with a fluorescent label material which preferentially binds to dental plaque, and the fluorescence emission of the label material at areas of the tooth at which it has bound is detected to indicate the presence of dental plaque. Patent publications WO 92/06671, U.S. Pat. No. 5,382,163, DE 29704185, DE 29705934, EP 0774235, and also WO 97/01298 (Phillips) disclose methods of this type and devices for performing these methods. GB 9810471.4 filed on 16 May 1998 and internationally filed as PCT/EP99/03273, the contents of which are included herein by way of reference, discloses a further method and apparatus for detecting biological deposits on tooth surfaces using fluorescence. One form of the apparatus disclosed in PCT/EP99/03273 comprises a toothbrush head having a bundle of optical fibres extending through it to direct incident radiation at a test tooth surface, and to collect emitted radiation from the test tooth surface.

It is usually a requirement of such methods that incident radiation is directed at the surface of the teeth under examination and that consequent fluorescence emission radiation from the surface of the teeth is collected. WO 98/1071 1 discloses a toothbrush provided with a head which is made of a monolithic body of an optically transparent materials for the purpose of directing light towards the surfaces of the teeth. In WO 98/10711 this radiation is for the purposes of therapy not for detection of biological deposits.

Those of the above-mentioned devices which are toothbrushes generally use bundles of optic fibres passing through the head and body of the toothbrush to both direct incident radiation to the head and collect emitted radiation from the head. It is an object of this invention to provide a toothbrush of the above-described type having an improved means for directing incident radiation onto the surface of teeth and for collecting radiation emitted from the surface of teeth in response to the incident radiation.

SUMMARY OF THE INVENTION

According to this invention a toothbrush head is provided having a bristle surface from which a cluster of bristles extends in a bristle direction, the head being suitable to direct incident radiation toward a surface of a tooth and to collect emitted radiation from the surface of the tooth, characterised in that the means to direct incident radiation toward the surface of a tooth, and/or the means to collect emitted radiation from the surface of the tooth comprise that the head is made at least in part of a material which is transparent to the incident and/or emit radiation.

DETAILED DESCRIPTION OF THE INVENTION

Suitably the material which is transparent to the incident and/or emitted radiation should be transparent to incident radiation in the wavelength range 400–520 nm, typically 470±40 nm, and to emitted radiation in the wavelength range above ca. 520 nm, typically in the range 530–600 nm. Adding these two ranges together, preferably the material is transparent over the range 400–630 nm. Suitable transparent materials include transparent plastics materials, such as polymethylmethacrylates (PMMA), polyacrylates (PA), polycarbonates (PC), polyethylene terephthalates (PET), polyesters, styrene acrylonitrile copolymers (SAN), polystyenes (PS), acrylonitrile butadiene styrene (ABS), polyamide polymers (PA) such as Nylon™ type materials, and other known transparent plastics. Suitable plastics ideally should not show fluorescence or other luminescence under the influence of the incident radiation.

In general, in the toothbrush for which the toothbrush head of this invention is provided directs the incident radiation toward a surface of the tooth in a direction generally parallel to the bristle direction, and is collected in the opposite direction. Generally the incident radiation is directed toward the surface of the tooth from part of the bristle surface. This enables the toothbrush to be held and used for brushing the teeth in a manner similar to that in which a conventional toothbrush is held and used. Generally it is preferred to locate the means to generate incident radiation and/or the means to associate this emitted radiation with the presence of biological deposits on the tooth within the handle of the toothbrush. These means will generally comprise electrical systems e.g. a light emitter and detector and associated electronics. Such a location in the handle is also convenient if the toothbrush is an electrical toothbrush, i.e having electrical drive means to move the cleaning bristles in a tooth cleaning operation. Generally if the means to generate incident radiation is located in the handle of the toothbrush, this incident radiation will be initially directed through the head in a direction substantially parallel to the longitudinal axis. If, as is common in toothbrushes, the bristle direction is substantially perpendicular to the longitudinal axis it will consequently be necessary to divert the radiation from a direction substantially parallel to the longitudinal axis into a direction substantially perpendicular to the longitudinal axis, i.e. into the bristle direction, and vice versa with the emitted radiation.

In a first embodiment of this invention the head of the toothbrush may be made of a monolithic body of a material which is transparent to the incident and/or emitted radiation and may thus guide radiation transmitted internally within it.

In such a construction incident radiation may be contained within the body of material by total internal reflection caused by the difference in refractive index ("N") between the high refractive index of the mass and the lower refractive index of the surrounding air of the environment.

Suitable materials from which such a monolithic body may be constructed include the above-mentioned transparent plastics materials.

In this first embodiment the head may be shaped so that its shape diverts incident and emitted radiation in the above-mentioned manner. For example an end surface of the head remote from the handle, or intermediate surfaces located between this end surface and the handle, may be curved or may be angled relative to the longitudinal direction and bristle direction so as to reflect, refract or otherwise divert incident radiation passing in the longitudinal direction along the head into the bristle direction. Additionally or alternatively the material may be coated, either wholly or partially, with a reflective coating, e.g. a thin reflective metal layer, so as to reflect incident radiation passing in the longitudinal direction along the head into the bristle direction. The shape and size of such surfaces, and/or of the reflective coating may be used to determine the area onto which incident radiation is directed and from which emitted radiation is collected. Additionally or alternatively the material itself or the above-mentioned reflective coating may be covered with a non-transparent layer, for example to prevent loss of incident or emitted radiation, or entry of extraneous radiation. If such a toothbrush head is manufactured by the usual process of injection moulding, then care should be taken to ensure that there is no formation of cloudiness, streaks or bubbles which might interfere with the transmission of radiation through the head material.

In this first embodiment of the toothbrush head the toothbrush bristles may be fixed into the monolithic body, e.g. using known bristle fixing techniques.

In this first embodiment, particularly if the structure of the toothbrush head comprises the material which is transparent to the incident and/or emitted radiation, the head may also incorporate one or more additional radiation guiding means, for example one or more optical fibres (e.g. of known type), to direct incident and/or emitted radiation respectively to and from the tooth surface. For example one or more such means, e.g. optical fibres may extend through the bristle surface and may direct incident radiation to the tooth surface, and the transparent material may collect emitted radiation through the bristle surface. Alternatively for example the transparent material may direct incident radiation to the tooth surface, and one or more such means, e.g. optical fibres extending through the bristle surface may collect emitted radiation. Alternatively for example such optical fibre(s) may end in the transparent material below the surface of the head, for example such fibre(s) may end below the bristle surface and facing in the bristle direction. Incident radiation may consequently pass through a transparent layer or window of the head after leaving the end of the fibre, and may then reach the tooth surface. Additionally or alternatively emitted radiation from the tooth surface may consequently pass through a transparent layer or window of the head material before reaching the end of the fibre.

In a second embodiment of this invention the head of the toothbrush comprises one or more cores of a material which is transparent to the incident and/or emitted radiation, which may guide radiation transmitted internally within it, and having a refractive index N1, the core being surrounded by a sheath which is also of material which is transparent to the incident and/or emitted radiation, the sheath having a refractive index N2, N1 being greater than N2, such that internal reflection occurs as a result of the difference in refractive index between N1 and N2 to direct radiation within the core.

Generally any difference between the refractive index of the core and a surrounding sheath of a transparent material can result in internal reflection within the core and consequently the desired guiding of radiation within the core. Suitable materials from which the core and sheath may be constructed include the above mentioned transparent plastics materials, and these may be selected for the core and sheath on the basis of differences in their known refractive index. For example suitable combinations of sheath and core materials are; sheath polyamide - core polyamide, polymethylmethacrylate, polycarbonate, polyethyleneterephthalate or polybutyleneterephthalate; sheath polymethylmethacrylate-core polyamide, polymethylmethacrylate, polycarbonate, polyethyleneterephthalate or polybutyleneterephthalate; sheath polycarbonate-core polyamide, polymethylmethacrylate, polycarbonate, polyethyleneterephthalate or polybutyleneterephthalate; sheath polyethyleneterephthalate-core polyamide, polymethylmethacrylate, polycarbonate, polyethyleneterephthalate or polybutyleneterephthalate; sheath polybutyleneterephthalate-core polyamide, polymethylmethacrylate, polycarbonate, polyethyleneterephthalate or polybutyleneterephthalate. From this list it is seen that polymers which are chemically similar but which are of for example diferent grades so as to have differing refractive indexes N2, N1 being greater than N2 may be used.

One example of such a combination is a core material is a PMMA, typically of refractive index N1 of ca. 1.7 combined with a sheath material which is a PET, typically of refractive index N2 of ca. 1.54.

In a preferred construction the sheath may comprise a monolithic body of the transparent material which forms the principal structure of the toothbrush head, e.g. the structure into which the bristles are fixed. Alternatively the core(s) and sheath may themselves be encased within the toothbrush head, for example being encased within a material which comprises the structure of the toothbrush head.

Additionally the core(s), and or the head itself may be coated, either wholly or partially, with a reflective coating, e.g. a thin reflective metal layer, so as to reflect incident radiation passing in the longitudinal direction along the head into the bristle direction.

Such a reflective layer may comprise the principal cause of internal reflection within the core. Therefore in a third embodiment of this invention the head of the toothbrush comprises one or more cores of a material which is transparent to the incident and/or emitted radiation, which may guide radiation transmitted internally within it, the core being surrounded by a sheath which is of material which reflects the incident and/or emitted radiation, such that internal reflection occurs within the core so as to direct incident radiation passing in the longitudinal direction along the head into the bristle direction.

Suitable materials from which the core and sheath may be constructed include the above mentioned transparent plastics materials. Suitable reflective materials include metals, such as a thin shiny layer of a metal such as aluminium or silver etc. in the form of an applied layer or foil applied to the outer surface of the core.

The cores described in the above-mentioned embodiments may direct either incident radiation, or emitted radiation, or both incident and emitted radiation. The core(s) may be shaped so that its/their shape diverts incident and emitted radiation in the above-mentioned manner. For example a surface of the core(s) remote from the handle, or intermediate surfaces located between the end surface of the core remote from the handle and the handle may be curved or may be angled relative to the longitudinal direction and bristle direction so as to reflect, refract or otherwise divert incident radiation passing in the longitudinal direction along the head into the bristle direction.

The core(s) may have a cross section which is determined experimentally to be sufficient that a useful intensity of incident and emitted radiation may be transmitted along their length. For example the core(s) may have any convenient cross sectional shape, e.g. circular, oval, rectangular with rounded ends or corners etc. The cross sectional dimensions of the core may be determined by experiment, but for convenience may typically be 5–95%, e.g. 10–50%, of the cross sectional width and/or thickness of the head.

The core may have a surface which is substantially perpendicular to the bristle direction, so that incident radiation passing along the core may emerge from the core through this surface and from thence be directed to the tooth surface. Conversely emitted radiation from the tooth surface may enter the core through this surface and may be directed through the core. For example the core(s) may be a generally "L" shaped structure having a limb oriented in the generally longitudinal direction of the head, i.e. perpendicular to the bristle direction, and a limb oriented in the bristle direction and terminating in a surface which is substantially perpendicular to the bristle direction. The bend of the "L" between the limbs may be curved e.g. in a spherical geometry, or bevelled e.g. to present a surface at 45° to the limbs.

The core(s) may extend through the sheath material so that the core(s) is/are exposed outside of the toothbrush head so that radiation may pass directly from the core to the tooth surface and vice versa. Alternatively radiation passing into or out of the core may need to pass through the sheath material, or through other parts of the toothbrush head on its way to and from the tooth surface.

The above-mentioned transparent plastics materials from which the toothbrush head, e.g. the body, sheath and core, may be made can be formed using known techniques of injection moulding, as are well known in the toothbrush art. It is important to maintain transparency in these materials, and if the core and sheath are formed by injection moulding, then care should be taken to ensure that there is no formation of cloudiness, streaks or bubbles etc. which might interfere with the transmission of radiation through the core or sheath.

In a suitable manufacturing process for a toothbrush of the invention having a core, the core may be made first, e.g. by injection moulding. The formed core may then be positioned in a second injection mould cavity defining the shape of the sheath, which may be the monolithic body of the toothbrush head, and then the sheath may be moulded around the core by a second injection moulding process in this second cavity. In this last mentioned procedure care should be taken that the sheath and core materials have identical or similar shrinking values as they cool after the injection moulding process to ensure that no cracks form due to differential contraction.

Accordingly the invention also provides an injection moulding process in which a toothbrush head or a core for a toothbrush head, as described above are made.

Accordingly the invention also provides an injection mould suitable for use in such an injection moulding process.

A reflective metal layer may be in the form of a foil which can be attached to a pre-formed head or core component during the manufacturing process. If for example such a reflective metal layer is attached to a pre-formed core, around which the head or a sheath is formed by a subsequent injection moulding step, care should be taken to ensure that the metal layer does not become loosened, detached or distorted during the moulding formation of the head material. Alternatively other known deposition technologies may be used to deposit such a metallic layer.

In a preferred embodiment of the invention one or more thin radiation-guiding filaments made of a material which is transparent to the incident and/or emitted radiation, e.g. at the wavelength ranges referred to above, e.g. optical fibres may be used to guide radiation from the toothbrush head to the tooth surface and in the reverse direction. Such filaments may typically have a cross section of ca. 0.25 mm. In one form of this embodiment one or more of the toothbrush bristles may comprise such (a) radiation guiding filament(s), toothbrush bristles typically having a cross section of 0.12–0.25 mm. Suitable materials from which such filaments may be made are known, and include the plastics materials referred to above. Although such filaments may be made of single materials, such as are typically used for toothbrush bristles, it is preferred for the function of radiation guiding that the filaments should comprise an inner core of a material transparent to the incident and/or emitted radiation enclosed within a sheath, i.e. an enclosing layer, with the properties of the core and sheath being such that internal reflection occurs within the core to guide the radiation along the sheath. For example the core and sheath of the filament may be materials which are both transparent to the radiation, and the core may have a lower refractive index than the sheath, in a manner similar to that described above, such that internal reflection occurs as a result of the difference in refractive index between the core and sheath to direct radiation within the core. Suitable combinations of transparent materials for the filament core and sheath are as described above. Methods are known for making filaments in the form of a core and sheath are known, for example in WO97/14830 and in PCT/EP98/00718 where the inner core may be a soft elastomer and the sheath may be a harder plastic material. Alternatively the filament core may be transparent and the sheath may be a reflective material such as a shiny metal layer, which may be applied by known deposition techniques.

When one or more filaments such as bristles are used in this way it is necessary that a good optical connection is made between the head and the filament(s). Such a connection may be made between the filaments and e.g. the sheath material of the head, e.g. a monolithic structural material, or a core within the head. This may be accomplished in a number of ways.

If radiation guiding filaments such as bristles are used in this way it is preferred that the ends of the bristles which are fixed into the toothbrush head are fixed into the toothbrush head in a manner which allows radiation to pass from the toothbrush head or core(s) within the toothbrush head into the bristles and vice versa. For example the bristles may be fixed into the head by means of a process of welding, or by fixing into a bed of a liquid hardenable substance, so that a good optical connection is made between the head and the bristle. Suitable processes to achieve this are known in the state of the art, for example WO 95/31917 and WO 97/39649. In such a welding process the ends of individual bristles or bundles of bristles which are to be fixed into the toothbrush head may be thermally fused so that a "mushroom head" is formed in the toothbrush head. Furthermore if the mushroom head is formed in this way care should be taken that the mushroom head and/or the adjacent ends of the bristles do not become opaque or translucent but remain transparent to the exciting radiation and/or emitted fluorescence radiation. Some such known processes, e.g. that of WO 97/39649 may enable bristles to be fixed into the head with fixed ends which have end surfaces which are generally perpendicular to the length direction of the bristles, facilitating transmission of light from the head material to the bristles.

Alternatively the toothbrush bristles may alternatively be fixed into the toothbrush head in the conventional manner in which a number of bristles folded in two lengthwise then a small metal clip or "anchor" is fastened around the bundle so formed, and the clip is jammed into a fixing hole in the toothbrush head. In this case it may be necessary to cut, polish or grind the region of the fold so that a good optical connection is made between the head and the bristle.

If however bristles are present on the head of the toothbrush of the invention which are not used for radiation guiding but simply perform the conventional function of cleaning the teeth, these may be fixed to the head by known techniques, without the need for optical connection to the head.

In one preferred construction the above-mentioned light guiding filaments are optically connected to the above-mentioned core(s), for example being fixed onto or into the core. For example the core may be made of the above described transparent plastic material having a surface facing in the bristle direction, and the ends of the filaments may be fixed onto or into this surface. For example the surface of the core may be constructed to mate closely with the ends of the filaments and these ends may be bonded into optical, e.g. physical, contact with the surface of the core. Preferably however the ends of the bristles are fixed into the core by embedding the ends into the core material whilst this is in a soft fluid state and allowing the core material to subsequently harden. This may be achieved for example with a core made of a plastic material that can be moulded into shape in a fluid form. e.g. a thermoplastic plastic, and the fluid plastic material of the core is allowed to flow around the ends of the bristles (whilst holding them in a suitable configuration) and then solidify. If this is done with the plastic material of the core in a hot fluid state, the bristle material may also fuse with the core material to form a very intimate bond between the bristles and the core. Techniques, e.g of injection moulding for fusing filaments suitable for toothbrush bristles into thermoplastic materials are well known in the art. For example if the core(s) is/are of the generally "L" shape described above the filaments may be fixed to or into the surface which is substantially perpendicular to the bristle direction, e.g. the end of a limb of an "L" shaped core which points in the bristle direction.

Such radiation guiding filaments may be bundled together into tufts each including a plurality of such filaments. One or more tufts may be connected to each core. Such tufts may be circular in cross section, e.g. corresponding approximately to the cross section of conventional toothbrush cleaning bristle tufts, or alternatively the cross section of the tuft may correspond to that of a none circular cross sectioned core.

Additionally or alternatively the toothbrush head may be provided with other radiation guides to guide radiation to and from the tooth surface to the toothbrush head. For example the bristle surface may be provided with one or more bristle free areas which function as windows for radiation passing to and from the tooth surface to the toothbrush head. For example additionally or alternatively the toothbrush head may be provided with lenses for radiation passing to and from the tooth surface to the toothbrush head which focus emitted radiation from the toothbrush head onto the tooth surface and/or which focus or collect emitted radiation from the tooth surface toward the above-mentioned radiation guiding means or the above-mentioned core.

Suitable materials for such radiation guides, lenses, windows etc. are transparent materials which are transparent to the incident and/or emitted radiation include known transparent plastic materials, such as those referred to above. If the bristles of the toothbrush are to be used as radiation guides then these should be made of fibre materials which are sufficiently transparent to the incident and/or emitted radiation of interest.

Suitably in the toothbrush for which the head of this invention is intended he incident radiation may be of a wavelength known from the state of the art referred to above which excites fluorescence emission from biological deposits on tooth surfaces, and/or from deposit-free tooth surfaces, and the emitted radiation may be of a wavelength known from the state of the art to correspond to fluorescence emission from such surfaces. Suitably the incident radiation may have a wavelength between 430 and 500 nm and the emitted radiation may have a wavelength above 520 nm. Although incident radiation of wavelength below 430 nm may be more effective at exciting fluorescence emission from biological deposits or tooth surfaces than higher wavelength radiation, this lower wavelength radiation may be harmful to mouth tissues.

The toothbrush for which the head of this invention is intended is also provided with means to generate incident radiation and to direct this incident radiation toward the surface of a tooth. This may comprise a suitable radiation source, for example a light emitting diode of known type. The means to associate the emitted radiation with the presence of biological deposits on the tooth may comprise a conventional detector e.g. a semiconductor photodiode. It may be appropriate to incorporate optical filters, e.g. dichroic mirrors, into the optical path between the detector and the test tooth surface to ensure that emitted radiation of a suitable wavelength is preferentially received by the detector. These means, and an appropriate power supply, electronic processing devices, and means to signal the presence and/or absence of biological deposits on a tooth surface may conveniently be provided within the handle of the toothbrush. Suitable means for these purposes will be apparent to those skilled in the art, and are disclosed in the state of the art.

Conveniently the head of the toothbrush of the invention may be made detachable from the handle of the toothbrush for which it is intended. This is particularly convenient if the handle, as described above, includes the radiation source etc., so that the head can be replaced when for example its bristles become worn out without the need to also replace these relatively expensive electrical components. If the head of the toothbrush is detachable from the handle the joint between the head and handle should comprise an optical connector.

In a further aspect the present invention also provides a toothbrush provided with a head as described above.

Such a toothbrush may comprise a handle by which it may be held, and having a head from a bristle surface of which a cluster of bristles extends in a bristle direction, the head and handle being disposed along a longitidinal axis, the toothbrush being provided with means to generate incident radiation and to direct this incident radiation toward the surface of a tooth, and being provided with means to collect emitted radiation from the surface of the tooth and to associate this emitted radiation with the presence of biological deposits on the tooth, characterised in that the means to direct incident radiation toward the surface of a tooth, and/or the means to collect emitted radiation from the surface of the tooth comprise that the head is as described above.

The toothbrush head and toothbrush of the present invention is particularly suited for use with or as the device and method disclosed in GB 9810471.4 filed on 16 May 1998, and internationally filed as PCT/GB99/03273 the contents of which are included herein by way of reference. The device disclosed therein is for detecting biological deposits on the surface of a tooth, and comprises;

illumination means to direct exciting radiation onto a test tooth surface, detection means to detect fluorescence emission from the rest tooth surface at a wavelength associated with that of auto fluorescence emission from a substantially biological deposit- free tooth surface, means to make a comparison of the intensity of the said fluorescence emission from the test tooth surface with an intensity of auto fluorescence emission, at a wavelength associated with that of auto fluorescence emission from a substantially biological deposit free tooth surface, from a tooth surface known to have less biological deposit thereon than is present at the test tooth surface, means to associate the comparison thus obtained with the presence of biological deposits on the test tooth surface, and, indicator means to indicate the presence of such biological deposits to a user of the device.

BRIEF DESCRIPTION OF THE FIGURES

The toothbrush head, toothbrush, processes and moulds of this invention will now be described by way of example only with reference to the accompanying figures, of which.

Figure 1:
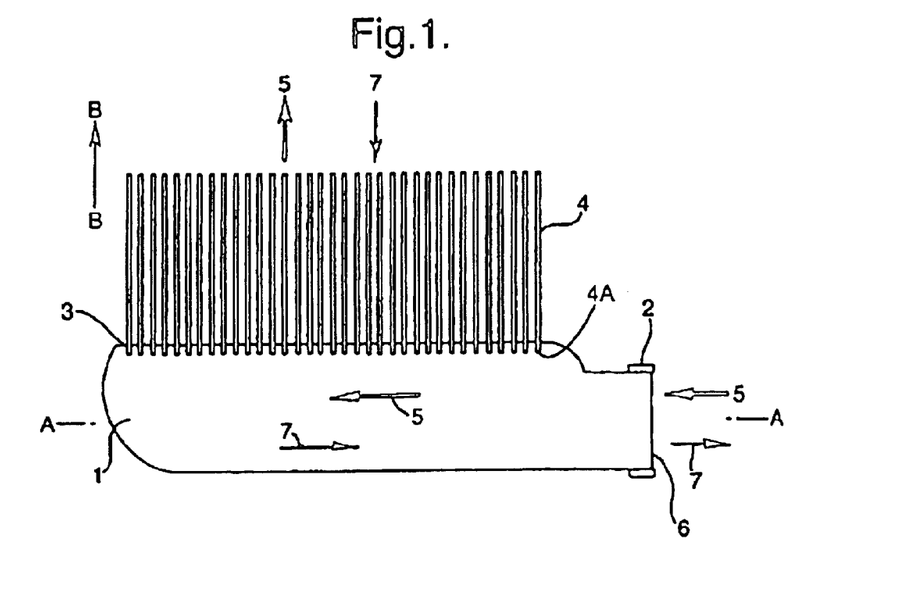
FIGS. 1 to 9 show longitudinal sections through heads of toothbrushes of this invention.

Referring to FIG. 1 a toothbrush head 1 is shown. The head is detachably connectable to a handle (not shown) by means of connector means 2, which may be conventional in the art. The head 1 and the toothbrush handle are disposed along a longitudinal axis A-A. From a bristle surface 3 of the head 1 extends a cluster of bristles 4, extending in a bristle direction B-B. The head 1 is made of a mass of plastic material which is transparent to radiation in the wavelength region at least between 400–600 nm. The ends 4A of the bristles 4 which are fixed into the head 1 are welded into the head 1 material as individual filaments by a state of the art process.

Incident radiation may be directed from a source (not shown in FIG. 1) into the head 1 from the direction of the handle, i.e. in the direction shown by the arrow 5, by means of an optical connection surface 6, being a planar surface of the transparent material of which the head 1 is made. Because of internal reflection within the transparent head resulting from the difference in refractive index between the high refractive index $N_1$ of the head material and the lower refractive index $N_2$ of the surrounding air, this radiation is directed through the head 1 and emerges from the head 1 via the bristle face 3, i.e. substantially in the bristle direction B-B. The radiation emerging from the bristle face 3 impinges upon the surface of a tooth (not shown) and excites fluorescence emission from biological deposits on the tooth surface and/or deposit-free tooth surfaces. This emitted radiation traveling in the direction shown by the arrow 7 passes through the bristle face 3 and is collected by the transparent head 1. As before, internal reflection within the transparent head, causes the emitted radiation to be directed in the direction toward the handle, i.e. in the direction 7.

Figure 2:
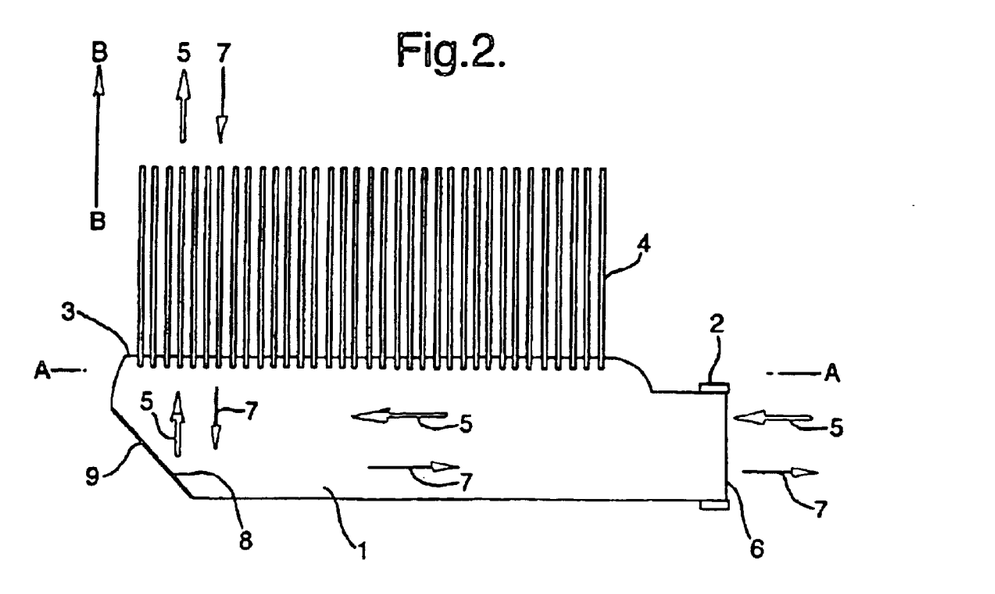

Referring to FIG. 2, features common in construction with FIG. 1 are numbered correspondingly. In this embodiment an end surface 8 of the head 1 remote from the handle is angled relative to the longitudinal direction A-A and bristle direction B-B so as to reflect incident radiation passing in the longitudinal direction A-A along the head 1 into the bristle direction B-B. This end surface 8 is coated with a reflective coating 9, being a thin reflective metal layer, so as to reflect incident radiation passing in the longitudinal direction along the head into the bristle direction. The coating 9 is a thin reflective metal foil applied to the head material 1 by hot stamping. As in the embodiment of FIG. 1 the radiation emerging from the bristle face 3 impinges upon the surface of a tooth (not shown) and excites fluorescence emission from biological deposits on the tooth surface and/or deposit-free tooth surfaces. This emitted radiation traveling in the direction shown by the arrow 7 passes through the bristle face 3 and is collected by the transparent head 1 and is reflected at the surface 8 along the longitudinal direction A-A toward the handle. As before, internal reflection within the transparent head, causes the emitted radiation to be directed in the direction toward the handle, i.e. in the direction 7A.

Figure 3:
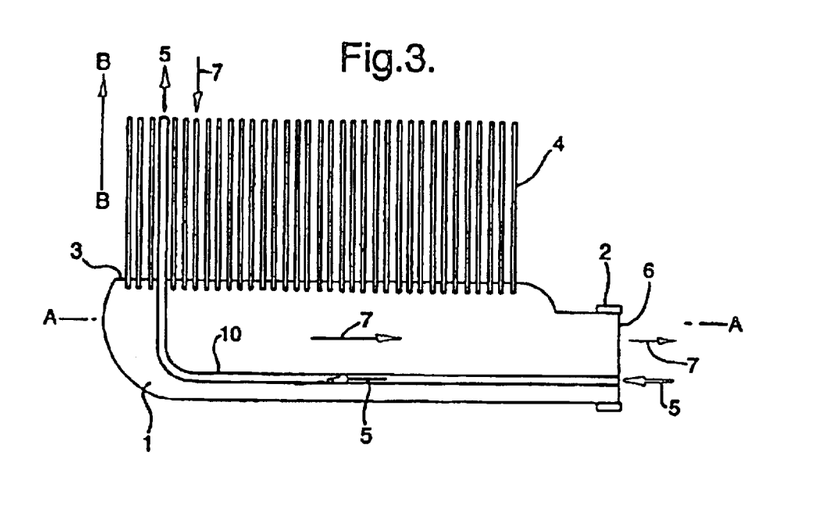
Figure 4:
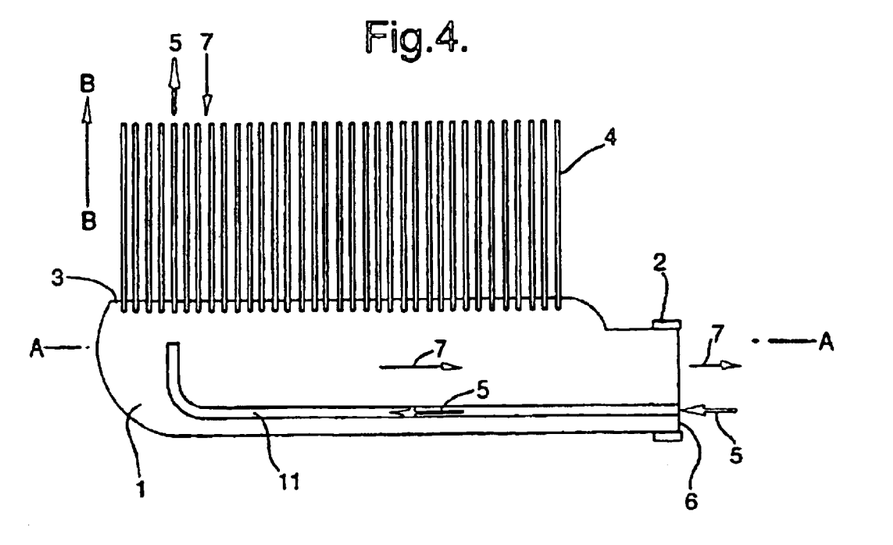
Figure 5:
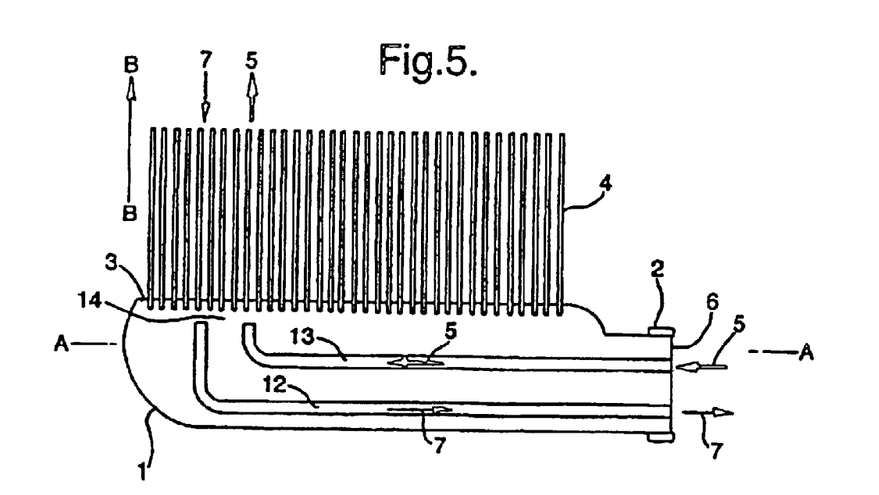

Referring to FIGS. 3, 4 and 5, features common in construction with FIG. 1 are numbered correspondingly. Within the mass of transparent material of the head 1 are located optical fibres 10, 11, 12, 13 of conventional type.

These fibres 10, 11, 12, 13, direct incident and/or emitted radiation respectively to and from the tooth surface. As shown in FIG. 3 an optical fibre or bundle of optical fibres 10 extends through the surface of the transparent mass 1 in the bristle direction B-B and directs incident radiation to the tooth surface (not shown) in the direction shown by the arrow 5. The mass of transparent material 1 collects emitted radiation, and as described with reference to FIGS. 1 and 2 directs this emitted radiation back in the direction of the handle, i.e. the direction shown by arrow 7. Alternatively the mass of transparent material 1 may direct incident radiation to the tooth surface, and the optical fibre(s) 10 extending through the surface of the mass may collect emitted radiation and direct it back toward the handle.

As shown in FIGS. 4 and 5, optical fibres or bundles of optical fibres 11, 12, 13 end in the mass of transparent material below the bristle surface, facing in the bristle direction B-B. Incident radiation passing in the direction of the handle consequently passes through a transparent layer or window 14 of the mass after leaving the end of the fibre(s), and may then reach the tooth surface. Similarly emitted radiation from the tooth surface passes through this transparent layer 14 before reaching the end of the fibre. In FIG. 4 a single fibre or bundle 11 is used to direct radiation from the direction of the handle toward the tooth surface, and the transparent mass of head material 1 collects the emitted radiation, or vice versa. In FIG. 5 two fibres or bundles are used, one to direct incident radiation toward the tooth surface and the other to collect emitted radiation and direct it toward the handle.

At surface 6 the optical fibres or bundles of fibres 10, 11, 12, 13 ends with a suitable optical connection surface.

Figure 6:
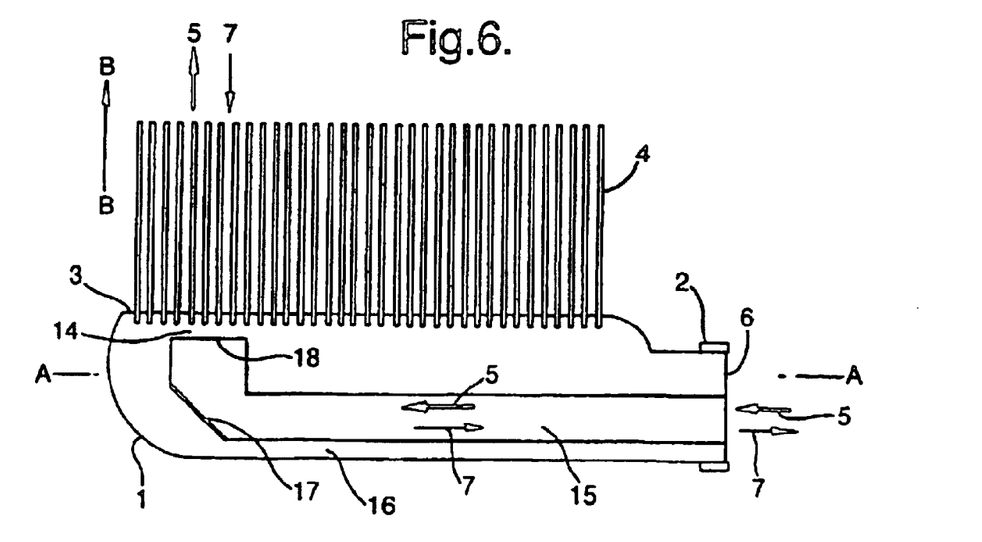

Referring to FIG. 6, features common in construction with FIG. 1 are numbered correspondingly. The head 1 of the toothbrush comprises a core 15 of material which is transparent to the incident and/or emitted radiation, which can guide radiation transmitted internally within it, and having a refractive index $N^1$. The core 15 may be made by injection moulding in a first moulding operation, and then the head 16 may be injection moulded around the core 15, care being taken during this second moulding operation to ensure that the so formed core 15 does not crack, soften, distort or otherwise become distorting to light transmission.

This core 15 extends within the head 1 of the toothbrush in the longitudinal direction A-A. The core 15 is surrounded by a sheath 16 which is also of material which is transparent to the incident and/or emitted radiation, the sheath having a refractive index $N^2$, $N^1$ being greater than $N^2$. Internal reflection occurs as a result of the difference in refractive index between $N^1$ and $N^2$ to direct radiation within the core, so that incident radiation passing in the direction 5 and collected emitted radiation passing in the direction 7 are contained within the core 15 and directed toward the handle. The sheath comprises a mass of material which forms the structure of the toothbrush head and from which the bristles 4 extend.

An end surface 17 of the core remote from the handle is angled relative to the longitudinal direction A-A and bristle direction B-B so as to reflect incident radiation passing in the longitudinal direction along the head into the bristle direction. Additionally the surface 17 may be coated with a reflective coating, being a thin reflective metal layer, e.g. a foil applied by hot stamping as above, so as to reflect incident radiation passing in the longitudinal direction along the head into the bristle direction. At its end 18 remote from the handle the core 15 ends with a surface which is substantially perpendicular to the bristle direction B-B, so that incident radiation passing along the core in direction 5 may emerge from the core through this surface and from thence be directed to the tooth surface. Similarly emitted radiation from the tooth surface is collected by the core 15 and directed toward the handle in direction 7. The incident and emitted radiation therefore passes through the layer 14 of transparent material of the head 1. At surface 6 the core ends with a suitable optical connection surface.

Figure 7:
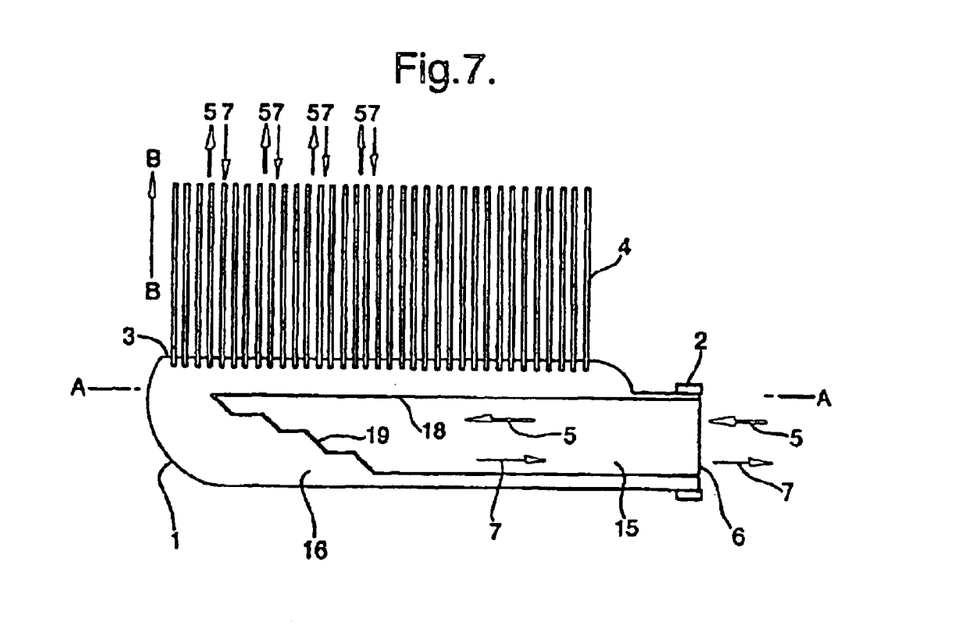

Referring to FIG. 7, features common in construction with FIG. 1 are numbered correspondingly. A toothbrush head has a core 15 surrounded by a sheath 16, with differing refractive indices, the sheath 16 having a refractive index $N^2$, the core 15 having a refractive index $N^1$ being greater than $N^2$, similar in construction and operation to that of FIG. 6. As shown in FIG. 7 there are a number of intermediate surfaces 19 which are angled relative to the longitudinal direction A-A and the bristle direction B-B so as to reflect incident radiation passing in the longitudinal direction along the head into the bristle direction. These intermediate surfaces 19 may be coated with a reflective coating.

The surface 18 of the core 15 is parallel to the bristle face, and perpendicular to the bristle direction B-B, and incident radiation and emitted radiation are respectively directed to and collected from the tooth surface through surface 18 and the transparent window layer 14. At surface 6 the core ends with a suitable optical connection surface.

Figure 8:
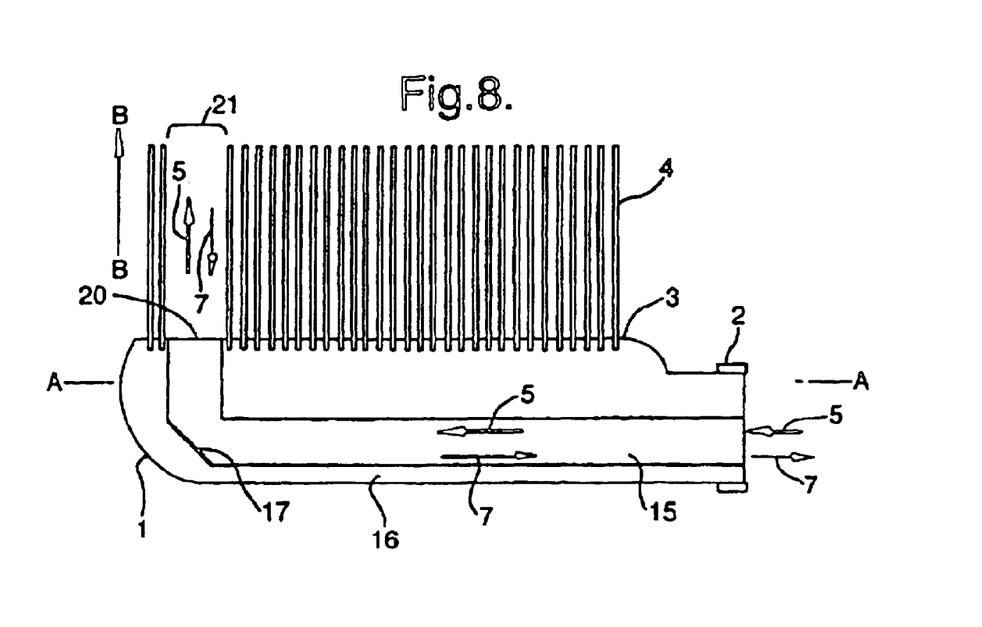

Referring to FIG. 8. features common in construction with FIG. 1 are numbered correspondingly. A toothbrush head 1 having a core 15 similar in construction and function to that shown in FIG. 6 is illustrated. In FIG. 8 the core 15 extends through the sheath material 16 so that the core is exposed at surface 20 outside of the toothbrush head 1 so that radiation may pass directly from the core to the tooth surface and vice versa. Additionally the toothbrush head 1 is provided with a bristle free area 21 which functions as a window for radiation passing to and from the tooth surface to the toothbrush head 1 into the core 15. At surface 6 the core ends with a suitable optical connection surface.

Figure 9:
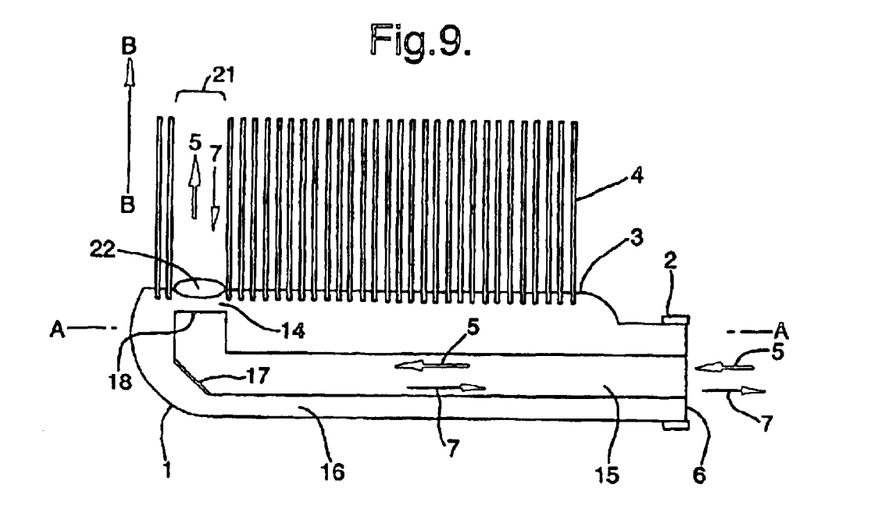

Referring to FIG. 9, features common in construction with FIG. 1 are numbered correspondingly. A toothbrush head 1 having a core 15 similar in construction and function to that shown in FIG. 6 is illustrated. In FIG. 9 the toothbrush head 1 is provided with a bristle free area 21 which functions as a window for radiation passing to and from the tooth surface to the toothbrush head 1 into the core 15. Additionally a lens 22 of transparent material is provided in the optical pathway between the end 18 of the core 15 and the tooth surface. This lens 22 focuses incident radiation emerging from surface 18 toward the tooth surface, and also assists the collection of emitted radiation from the tooth surface and the directing of this emitted radiation along core 15 toward the handle of the toothbrush. At surface 6 the core ends with a suitable optical connection surface.

Referring to FIGS. 10A, 10B, 10C, 101D and 10E constructions of bundles of bristles for a toothbrush head of this invention are shown in more detail.

Figure 10A:
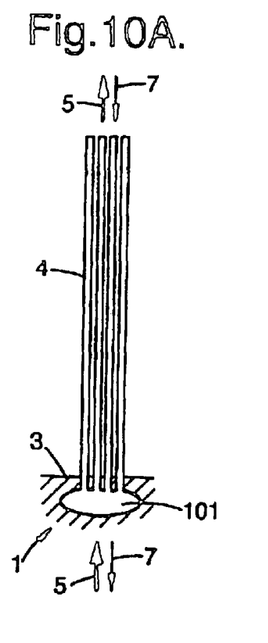
FIGS. 10A, 10B, 10C, 10D and 10E show cross sections through bundles of bristles of the toothbrush of this invention being used as radiation guides.
Figure 10B:
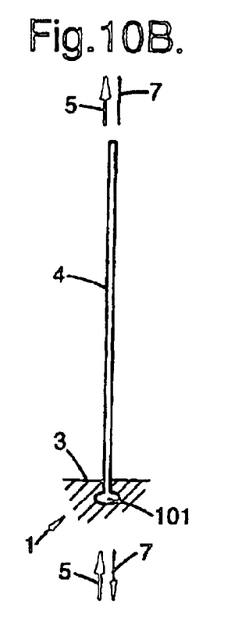

In FIG. 10A a bundle of bristle fibres 4, made of a fibre material which is transparent to incident radiation, has been fixed into the material of a toothbrush head 1 so that they extend from the bristle face 3 by means of a state of the art welding process which has melted the ends of the bundle of bristles 4 into a mass 101, which is itself fused with the material of the head 1. The fused mass 101 enables incident radiation to pass in the direction 5 from the head 1 material into the bristles 4, and emitted radiation to be collected in the opposite direction. The fused mass 101 may be shaped into a lens shape to assist in guiding radiation into and out of the bristles 4. In FIG. 10B an analogous situation is shown in which a single bristle or "monofilament" bristle is fixed into the toothbrush head, for example using a process as disclosed in WO 97/39649, and the end 101 of a single such bristle is fused into a lens shape.

Figure 10C:
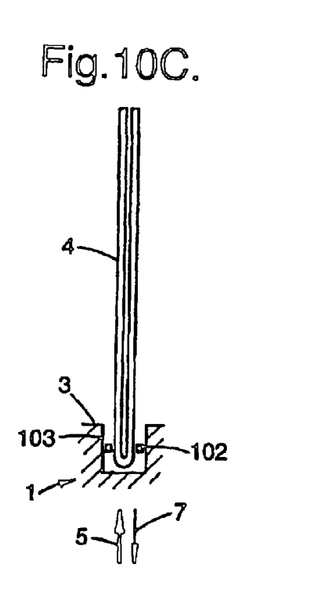
Figure 10D:
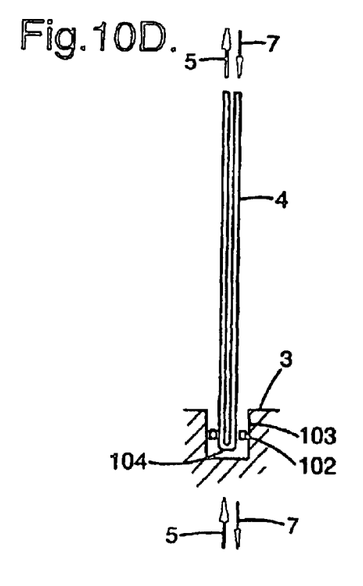

In FIGS. 10C and 10D bristles 4 are fixed into the toothbrush head 1 in the conventional manner by folding each bristle 4 in two and fastening a small metal clip or "anchor" 102 around the folded bristles near the fold. The anchor is then jammed into a fixing hole 103 in the bristle face. In FIGS. 10C and 10D only one of the bristles included in the bristle bundle is shown. As shown in FIG. 10C it is difficult for incident radiation and emitted radiation to pass in their respective directions 5 and 7 between the head 1 material and the bristle 4. In FIG. 10D the region 104 of the outside bend of the fold has been polished or ground, thereby creating a flat surface which facilitates transmission of incident and emitted radiation between the head 1 and bristles 4.

Figure 10E:
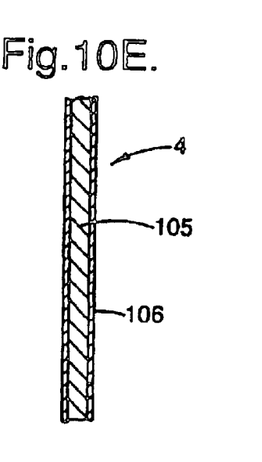

Referring to FIG. 10E a filament 4 is shown which comprises a core 105 made of a transparent plastic material, surrounded by a sheath 106 also of a transparent plastic material with a lower refractive index than that of the core 105. Alternatively the sheath 38 may be thin coating of a shiny metal, e.g. 2–3 microns thick. In such a filament internal reflection contains and guides radiation within and along the length of the filament. The filament 4 of FIG. 10E may form one of the filaments 4 of FIG. 10A or 10B, and may be used as a cleaning bristle.

Figure 11:
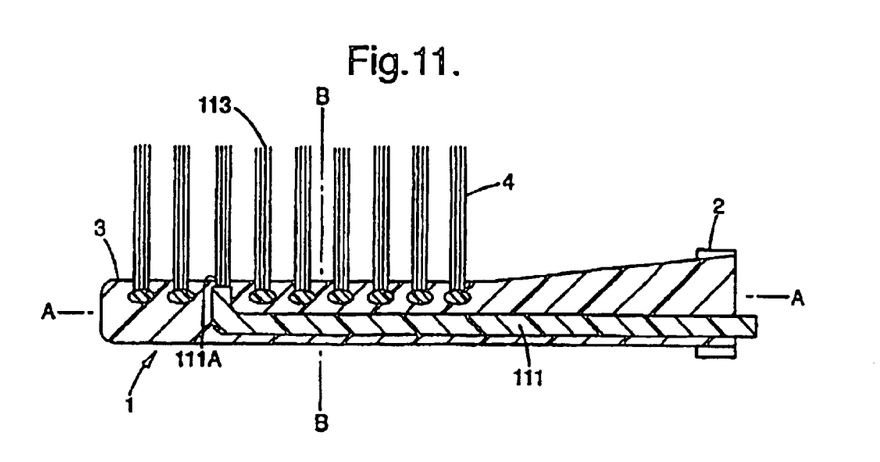
FIGS. 11 and 12 show further toothbrush beads of this invention.
Figure 11A:
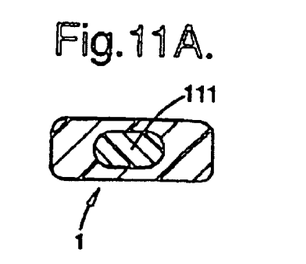
FIG. 11A shows a cross section through the head of FIG. 11, having a single core of a rectangular section with rounded ends.
Figure 12:
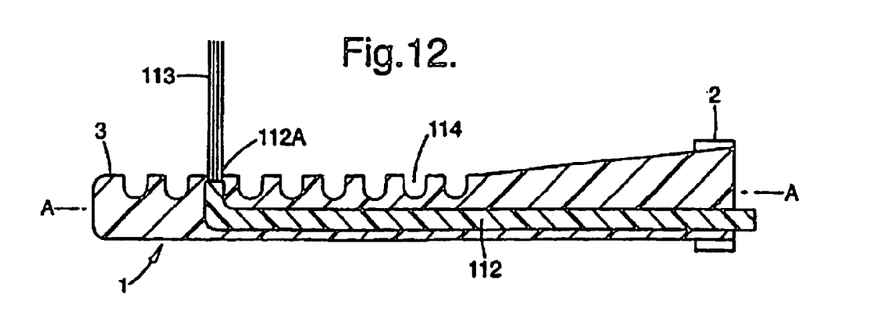
Figure 12A:
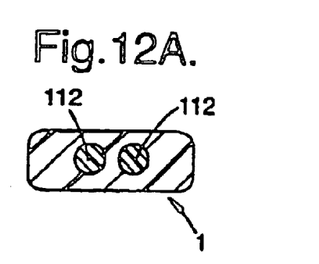
FIG. 12A shows a cross section through the head of the FIG. 12, having two cores of a circular section.
Figure 13:
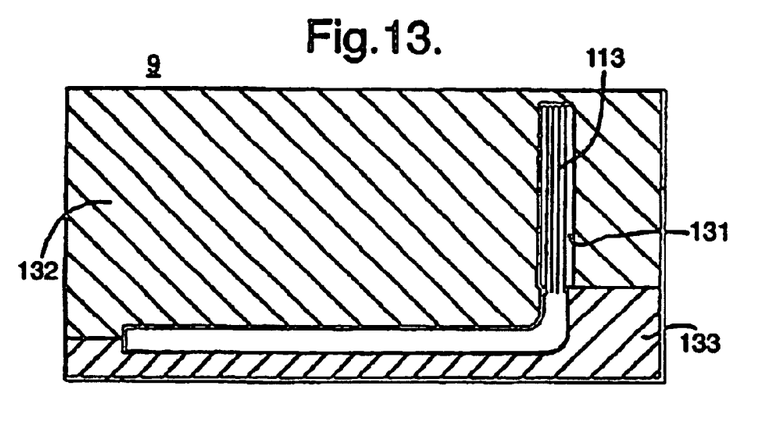
FIGS. 13–16 schematically show a process by which toothbrush heads of this invention may be manufactered.

Referring to FIGS. 11 and 12, two further forms of toothbrush head of this invention are shown. Parts in common with other toothbrush heads of the invention as shown in preceding figures are numbered correspondingly. In FIGS. 12 and 13 the toothbrush head 1 is made of a monolithic body of transparent plastic material, being polyethyleneterephthalate of refractive index 1.54. Within this head, in FIG. 11 is a single core 111, and in FIG. 13 two cores 112, being respectively as shown in FIGS. 11A and 12A of rectangular with rounded ends cross section (dimensions approximately 1.7×3.4 mm), and circular cross section. The cores 111, 112 are made of a transparent plastic material being polymethylmethacrylate of refractive index 1.71. In each of the toothbrush heads of FIGS. 11 and 12 the cores 111 and 112 are a generally "L" shaped structure having a limb oriented in the generally longitudinal direction A-A of the head, i.e. perpendicular to the bristle direction, and a limb oriented in the bristle direction and terminating in a surface 111A, 112A which is substantially perpendicular to the bristle direction. Into the surface 111A, 112A are fixed filaments 113. The filaments 113 are filaments of the type described and shown with reference to FIG. 10E, comprising a core and a sheath. The surface 111A, 112A terminates a short distance below the bristle surface 3 of the head 1.

Cleaning bristles 4 are also fixed into head 1. In FIG. 11 the tufts of bristles 4 are fixed in by the well known method of fusing their ends with the head material. In FIG. 12 the head 1 is provided with small holes 114 in its bristle face 3 into which bristles 4 (not shown) may be inserted and fixed using known types of small metal anchor.

Figure 11B:
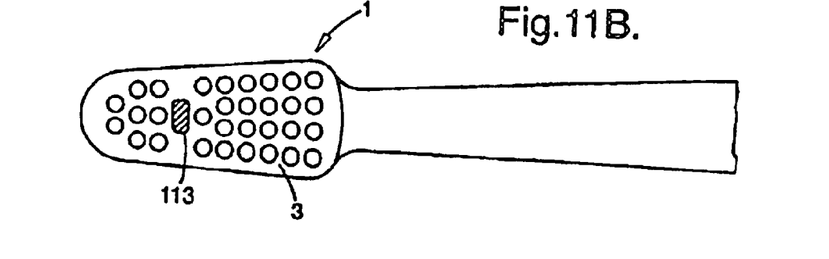
FIG. 11B shows a plan view of the bristle face of the toothbrush head of FIG. 11.
Figure 11C:
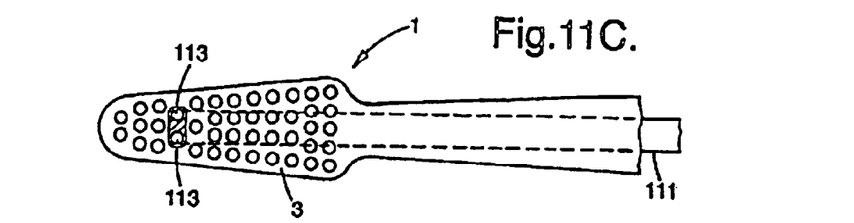
FIG. 11C show a plan view of the bristle face of an alternative construction of the head of FIG. 11.
Figure 12B:
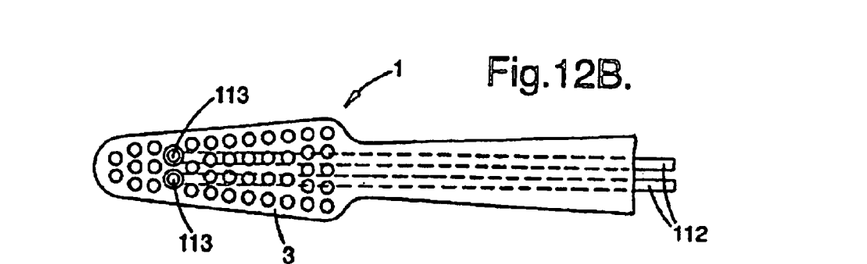
FIG. 12B shows a plan view of the bristle face of the toothbrush head of FIG. 12.
Figure 12C:
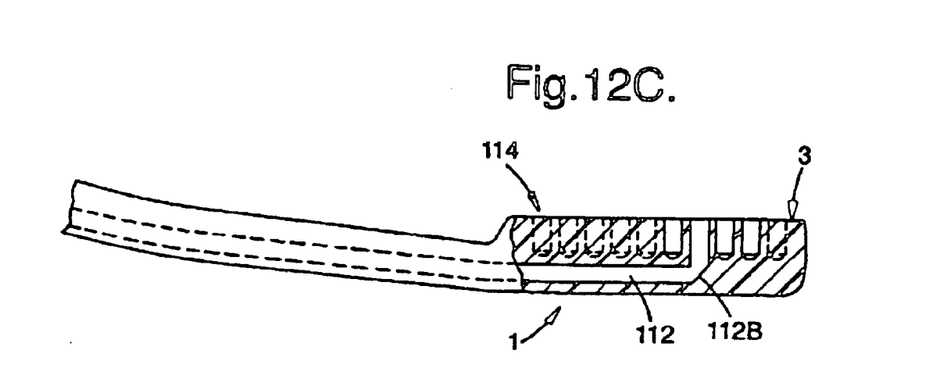
FIG. 12C shows a longitudinal section of an alternative construction of the head of FIG. 12.

FIG. 11B shows a plan view of the bristle face 3 of the toothbrush head 1 of FIG. 11, showing the generally rectangular cross section of the single tuft of light guiding filaments 113. FIG. 11C shows a plan view of the bristle face 3 of an alternative construction of the head 1 of FIG. 11, in which two generally circular cross sectioned tufts of light-guiding filaments 113 are fixed into the generally rectangular sectioned core 111. FIG. 12B shows a plan view of the bristle face 3 of the toothbrush head shown in FIG. 12, with one tuft of light-guiding filaments 113 fixed into each of the two cores 112. FIG. 12C shows an alternative construction of the head 1 of FIG. 12, in which the corner 112B between the two limbs of the "L" shaped core 112 is chamfered so as to be at ca. 45° to the alignment of the two limbs.

Referring to FIGS. 13, 14, 15 and 16 an injection moulding method and moulds are illustrated by which the toothbrush heads of FIGS. 11 and 12 may be made. Referring to FIG. 13, filaments 113 as used in the toothbrush head of FIG. 11 or 12 have been bundled into a bundle corresponding to the tuft 113 and have been inserted into a cavity 131 in part 132 of a two part injection mould. The mould is closed with the second part 133. Fluid polymethylmethacrylate resin is injected, via an injection port (not shown) into the mould cavity. Under the conditions of the injection the ends of the filaments 113 fuse with the resin. When the mould is cooled and opened the result is the structure shown in FIG. 14 being the "L" shaped core 111 or 112 with the embedded filaments 113.

Figure 14:
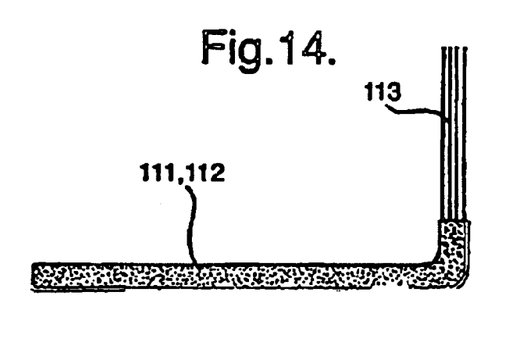
Figure 15:
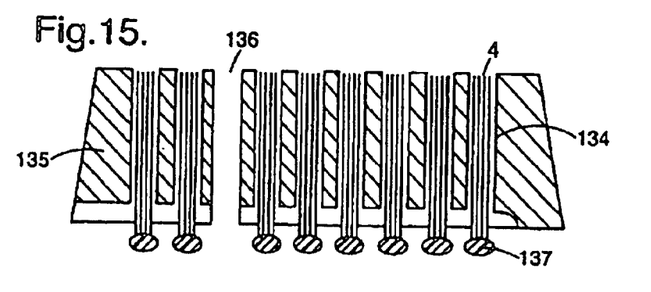
Figure 16:
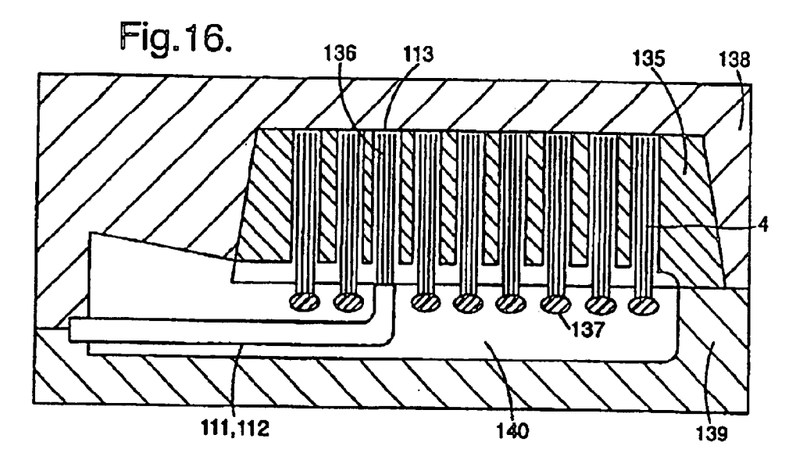

Meanwhile as shown in FIG. 15 cleaning bristles 4 are bundled and inserted into holes 134 in a mould cassette 135. A further hole 136 runs through the cassette 135. The ends of the bristles 4 are melted together by application of a hot surface (not shown) and allowed to cool so they solidify into fused masses 137 projecting from the holes. As shown in FIG. 16 the mould cassette 135 is assembled with parts 138, 139 of a further mould which includes a cavity 140 which defines the shape of the toothbrush head 1. During the assembly the core 111, 112 and filaments 113 as shown in FIG. 14 are also inserted into hole 136 in the cassette 135, so that the core 111, 112 lies within the cavity 140. Fluid potyethyleneterephthalate is injected into the cavity 140 via an injection port (not shown), with the result that the core 111, 112 and the bristles 4 become embedded in the so-formed toothbrush head 1. The above moulding operation has been described in its essentials, and numerous refinements of the technique are known which optimise such moulding operations.

Figure 17:
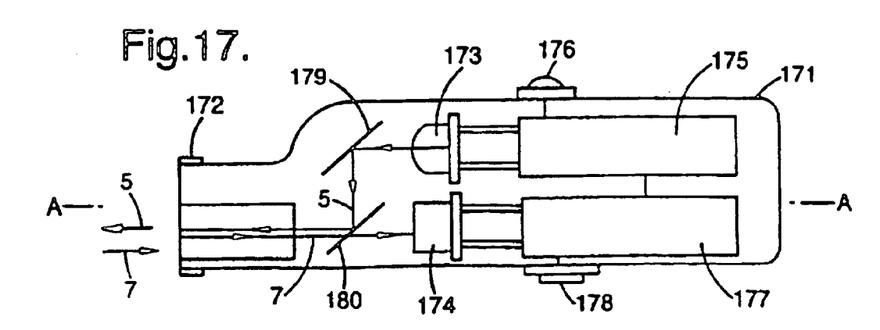
FIG. 17 shows a schematic longitudinal section through a handle of a toothbrush of this invention.

Referring to FIG. 17, a schematic diagram of the handle 171 of the toothbrush of this invention, suitable for use with the toothbrush heads of FIGS. 1–12 is shown. The toothbrush handle 171 is provided with a connector 172 enabling connection with the connectors 2 of the heads of FIGS. 1–12. The handle 171 includes an incident radiation source 173 being a light emitting diode of known type, for example capable of emitting radiation of a suitable wavelength. The handle 171 also includes a radiation detector 174 being a semiconductor photodiode. The handle 171 also includes a power supply 175, a control 176, electronic processing devices 177, and signaling means 178 to signal the presence and/or absence of biological deposits on a tooth surface, for example a light or buzzer etc. The toothbrush handle 171 also includes a set of dichroic mirrors 179, 180 which reflect incident radiation from source 173, but transmit emitted radiation so that these follow divergent radiation pathways. This enables the emitted radiation to be collected by the detector 174. Although illustrated in FIG. 17 for embodiments having a core 15, 112 corresponding constructions suitable for use with embodiments as in FIGS. 1–5 having monolithic heads and/or optical fibres will be apparent to those skilled in the art. The respective end surfaces of the handle 171 and a head e.g. as shown in FIGS. 1–12 should mate with precision such that there is as little loss of radiation as possible which passes between the head 1 and handle 171.

In use the toothbrush of the invention is used to brush the user's teeth, thereby aligning the bristle face 3 so that it faces the tooth surface at a convenient distance. The control 176 is operated, and incident radiation is directed in the direction 5 from the source 173, being reflected by dichroic mirrors 179, 180 onto a tooth surface using the toothbrush head 1 of this invention, for example via the filaments 113. Fluorescence radiation is emitted from the tooth surface, either from biological deposits such as plaque or from a deposit-free tooth surface or from both. This emitted radiation is collected by the head 1, e.g. again e.g via filaments 113 and directed back as described above to the detector 174, being transmitted through the dichroic mirror 180. An electrical signal is generated by the detector 174 and is processed by the processing device 177. The processing device 177 operates the signaling means 178 to indicate to the user the presence or absence of biological deposit.

What is claimed is:

1. A toothbrush head having a bristle surface from which a cluster of bristles extends in a bristle direction, the head comprising means to direct incident radiation toward a surface of a tooth and means to collect emitted radiation from the surface of the tooth, wherein;

the means to direct incident radiation toward the surface of a tooth, or the means to collect emitted radiation from the surface of the tooth comprise one or more core within the toothbrush head made of a first plastic material which is transparent to the incident or emitted radiation, and in which radiation transmitted internally within the core is guided by internal reflection within the core, the first plastic material having a refractive index $N^1$, and a first sheath surrounding the core and comprising a monolithic body in which the bristles of the head are mounted, and which is made of a second plastic material which is transparent to the incident or emitted radiation, the second plastic material having a refractive index $N^2$, $N^1$ being greater than $N^2$, such that internal reflection occurs as a result of the difference in refractive index between $N^1$ and $N^2$, or wherein the core is optionally surrounded by a second sheath which is of a reflective material which reflects the incident or emitted radiation.

2. The toothbrush head according to claim 1 wherein the first and second plastic materials are transparent over the wavelength range 400–630 nm.

3. The toothbrush head according to claim 1 wherein the reflective material is a metal.

4. The toothbrush head according to claim 1 wherein the head of the toothbrush is made of a monolithic body of the second plastic material and is coated with a reflective coating.

5. The toothbrush head according to claim 1 wherein the first plastic material is a polymethylmethacrylate and the second plastic material is polyethyleneterephthalate.

6. The toothbrush head according to claim 1 wherein the core is a generally "L" shaped structure having a limb oriented in the generally longitudinal direction of the head and a limb oriented generally in the bristle direction and terminating in a surface which is substantially perpendicular to the bristle direction.

7. The toothbrush head according to claim 6 wherein the bend of the "L" between the limbs is curved or bevelled to present a surface at 45° to the limbs.

8. The toothbrush head according to claim 1 wherein the cross-sectional dimension of the core is 5–95% of the cross sectional width and/or thickness of the head.

9. The toothbrush head according to claim 1 wherein the core has a surface which is substantially perpendicular to the bristle direction, so that incident radiation passing along the core may emerge from the core through this surface and from thence be directed to the tooth surface and/or emitted radiation from the tooth surface may enter the core through this surface and may be directed through the core, and a layer of transparent head material is provided at this surface so that incident and emitted radiation passes through this transparent head material.

10. The toothbrush head according to claim 1 wherein the bristle surface is provided with one or more bristle free areas which function as windows for radiation passing to and from the tooth surface to the toothbrush head.

11. The toothbrush head according to claim 1 further comprising one or more lenses for radiation passing to and from the tooth surface to the toothbrush head which focus emitted radiation from the toothbrush head onto the tooth surface and/or which focus or collect emitted radiation from the tooth surface.

12. A toothbrush having a head as claimed in claim 1.

13. An injection moulding process by which a toothbrush head as claimed in any one of the preceding claims is made, wherein the core is first made of the first plastic material, optionally a reflective metal layer is applied to this core, then the core is positioned in an injection mould cavity defining the shape of the monolithic body, and then the monolithic body is formed of the first second plastic material around the core by an injection moulding process.

* * * * *